US010093704B2

(12) United States Patent
Oganesyan et al.

(10) Patent No.: US 10,093,704 B2
(45) Date of Patent: Oct. 9, 2018

(54) EXPRESSION AND PURIFICATION OF CRM197 AND RELATED PROTEINS

(71) Applicant: Fina BioSolutions, LLC, Rockville, MD (US)

(72) Inventors: Natalia Oganesyan, North Potomac, MD (US); Andrew Lees, Silver Spring, MD (US)

(73) Assignee: Fina BioSolutions, LLC, Rockville, MD (US)

(*) Notice: Subject to any disclaimer, the term of this patent is extended or adjusted under 35 U.S.C. 154(b) by 2 days.

(21) Appl. No.: 15/114,642

(22) PCT Filed: Feb. 2, 2015

(86) PCT No.: PCT/US2015/014130
§ 371 (c)(1),
(2) Date: Jul. 27, 2016

(87) PCT Pub. No.: WO2015/117093
PCT Pub. Date: Aug. 6, 2015

(65) Prior Publication Data
US 2016/0333057 A1 Nov. 17, 2016

Related U.S. Application Data

(60) Provisional application No. 61/934,377, filed on Jan. 31, 2014.

(51) Int. Cl.
*A61K 39/00* (2006.01)
*A61K 39/385* (2006.01)
*A61K 39/02* (2006.01)
*A61K 39/40* (2006.01)
*A01N 63/00* (2006.01)
*A61K 48/00* (2006.01)
*C07K 14/34* (2006.01)
*C12P 21/02* (2006.01)
*A61K 39/05* (2006.01)
*C12N 15/74* (2006.01)
*G01N 33/68* (2006.01)

(52) U.S. Cl.
CPC ............ *C07K 14/34* (2013.01); *A61K 39/05* (2013.01); *C12N 15/74* (2013.01); *C12P 21/02* (2013.01); *G01N 33/6803* (2013.01); *C07K 2319/30* (2013.01)

(58) Field of Classification Search
CPC ......... C12P 21/02; C07K 14/34; A61K 39/05; C12N 15/74; G01N 33/6803
See application file for complete search history.

(56) References Cited

U.S. PATENT DOCUMENTS

2004/0043468 A1 3/2004 Mauro et al.
2004/0063187 A1 4/2004 Roemisch et al.
2006/0030022 A1 2/2006 Beckwith et al.
2007/0254334 A1 11/2007 Beckwith et al.
2011/0287443 A1* 11/2011 Retallack ............... C07K 14/34 435/7.1
2015/0184215 A1* 7/2015 Hsu ........................ C07K 14/34 435/69.1

FOREIGN PATENT DOCUMENTS

| JP | 2012-531198 | 12/2012 |
|----|-------------|---------|
| JP | 2013-529064 | 7/2013 |
| WO | WO 2007/063129 | 6/2007 |
| WO | WO 2010150230 | 12/2010 |
| WO | WO 2011/042516 | 4/2011 |
| WO | WO 2011/123139 | 10/2011 |
| WO | WO 2011/126811 | 10/2011 |
| WO | WO 2010/150230 | 12/2012 |
| WO | WO 2013/140335 | 9/2013 |
| WO | WO 2013/178974 | 12/2013 |

OTHER PUBLICATIONS

Tanito et al., Invest Ophthalmol Vis Sci., 2002; 43: 2392-2400.*
Zhao et al., Chinese Journal of Cellular and Molecular Immunology, Nov. 2003;19(6):585-7. (Year: 2003).*
Xiong et al., World Journal of Gastroenterology 2005; 11(7):1077-1082.
Stefan et al., Journal of Bacteriology 156:245-252 (2010).
Mahamad et al., Applied Genetics and Molecular Biotechnology 100:6319-6330 (2016).
Levy et al., Protein Expression and Purification 23:338-347 (2001).
EP Application No. 15 74 3243 Search Report dated Jun. 26, 2017.
EP Application No. 15 74 3243 Provisional Opinion Accompanying Search Report dated Jun. 26, 2017.
NZ Exam Report for PCT/US15/14130, dated Dec. 2, 2016.
Lobstein, J et al, "Shuffle, a novel *Escherichia coli* protein expression strain capable of correctly folding disulfide bonded proteins in its cytoplasm," Microbial Cell Factories, vol. 11, No. 753, DOI:10.1186/1475-2859-11-56.
EPO Supplemental Search Report dated Oct. 10, 2017.
EPO Written Opinion dated Oct. 10, 2017.
PCT Search and Patentability Report for PCT/US15/14130, dated Apr. 29, 2015.

(Continued)

Primary Examiner — Gary B Nickol
Assistant Examiner — Lakia J Jackson-Tongue
(74) Attorney, Agent, or Firm — Remenick PLLC

(57) ABSTRACT

The present invention is directed to the cells, compositions and methods for the production of recombinant protein. In particular, the invention is directed to a production process for obtaining high levels of soluble recombinant $CRM_{197}$ protein from *E. coli*. Cells preferably contain one or more mutations of disulfide reductase genes, so that disulfide reductase activity is reduced. The invention also relates to purification method for $CRM_{197}$ as well as characterization of properly folded $CRM_{197}$ protein.

Figure 1:
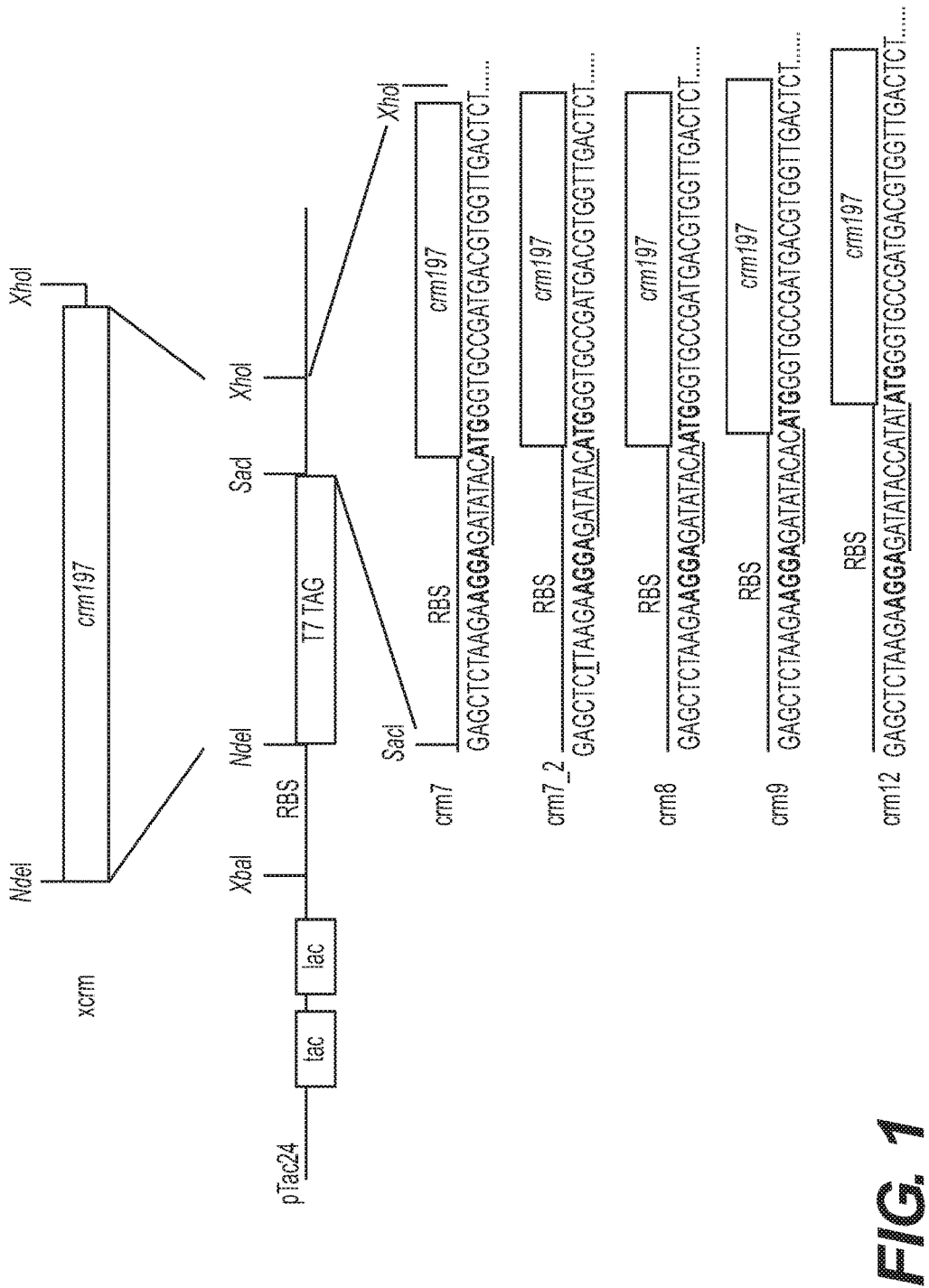

39 Claims, 2 Drawing Sheets
Specification includes a Sequence Listing.

(56) References Cited

OTHER PUBLICATIONS

AU Exam Report for PCT/US15/14130, dated Feb. 21, 2017.
NZ Exam Report for PCT/US15/14130, dated Apr. 24, 2017.
de Marco A "Strategies for successful recombinant expression of disulphide bond-dependent proteins in *Escherichia coli*" Microbial Cell Factories, vol. 8, No. 26, pp. 1-18.
Bessette PH et al "Efficient folding of proteins with multiple disulphide bonds in *Escherichia coli* cytoplasm" Proceedings of the National Academy of Sciences, vol. 96, No. 24, pp. 13703-13708.
Samuelson JC et al "Disulfide-Bonded Protein Production in *E. coli*", Genetic Engineering & Biotechnology News, Tutorials, vol. 32, No. 3.
AU Exam Report for PCT/US15/14130, dated Mar. 31, 2017.
Aminian, M. et al., Protein Expression and Purification, 2007, vol. 51, pp. 170-178.
Cabiaux, V. et al., Molecular Microbiology, 1988, vol. 2, No. 3, pp. 339-346.
AU Exam Report for PCT/US15/14130, dated Jun. 6, 2017.
CA Exam Report for CA App. No. 2938251, dated May 25, 2017.
JP Examination Report for JP 2016-567466, dated Sep. 4, 2017.
JP Examination Report for JP 2016-567466, dated Sep. 4, 2017 (English Translation).
T. Uchida et al., Diphtheria Toxin and Related Proteins, the Journal of Chemistry, 218(11):3838-44. 1973.
EPO Examination Report for EP 15 743 243.6, dated Jun. 18, 2018.
JPO Examination Report for JP 2016-567466, dated Jul. 5, 2018.
JPO Examination Report for JP 2016-567466, dated Jul. 5, 2018 (Translation).
Ganesh P. Subedi et al., Overproduction of Anti-Tn Antibody MLS128 Single-Chain Fv Fragment in *Escherichia coli* cytoplasm using a novel pCold-PDI vector, Protein Expression and Purification, 82:197-204 (2012).
Mirella D. Lorenzo et al., Heterologous Production of Functional Forms of Rhizopus oryzae Lipase in *Escherichia coli*, Applied and Environmental Microbiology, 71(12):8974-8977 (2005).

\* cited by examiner

SEQUENCE LISTING

<160> NUMBER OF SEQ ID NOS: 17

<210> SEQ ID NO 1
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Glu Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300
```

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
        370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
            530                 535

<210> SEQ ID NO 2
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Pro Gly His Lys Thr Gln Pro Phe Leu His Asp Gly Tyr Ala Val
1               5                   10                  15

Ser Trp Asn Thr Val Glu Asp Ser Ile Ile Arg Thr Gly Phe Gln Gly
            20                  25                  30

Glu Ser Gly His Asp Ile Lys Ile Thr Ala Glu Asn Thr Pro Leu Pro
        35                  40                  45

Ile Ala Gly Val Leu Leu Pro Thr Ile Pro Gly Lys Leu Asp Val Asn
    50                  55                  60

Lys Ser Lys Thr His Ile Ser Val Asn Gly Arg Lys Ile Arg Met Arg
65                  70                  75                  80

Cys Arg Ala Ile Asp Gly Asp Val Thr Phe Cys Arg Pro Lys Ser Pro
            85                  90                  95

Val Tyr Val Gly Asn Gly Val His Ala Asn Leu His Val Ala Phe His
            100                 105                 110

Arg Ser Ser Ser Glu Lys Ile His Ser Asn Glu Ile Ser Ser Asp Ser
        115                 120                 125

```
Ile Gly Val Leu Gly Tyr Gln Lys Thr Val Asp His Thr Lys Val Asn
        130                 135                 140

Ser Lys Leu Ser Leu Phe Phe Glu Ile Lys Ser
145                 150                 155
```

<210> SEQ ID NO 3
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 gatatac                                                            7

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 gatatacca                                                          9

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatataccat at                                                     12

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any hydropathic residue
<220> FEATURE:
<221> NAME/KEY: MOD_RES
<222> LOCATION: (2)..(3)
<223> OTHER INFORMATION: Lys or Arg
<220> FEATURE:
<221> NAME/KEY: MOD_RES
<222> LOCATION: (4)..(4)
<223> OTHER INFORMATION: Any hydropathic residue
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (6)..(6)
<223> OTHER INFORMATION: Any hydropathic residue

<400> SEQUENCE: 6

Xaa Xaa Xaa Xaa Xaa Xaa
1               5

```
<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Lys Ile Arg Met Arg Cys Arg
1               5

<210> SEQ ID NO 8
<211> LENGTH: 1608
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgggtgctg atgatgttgt tgattcctct aagtctttcg tgatggaaaa tttctcgtcc      60
tatcacggta ccaagcctgg ctatgtggat agcattcaaa agggtattca aaaccgaag     120 tctggtaccc agggcaacta cgatgacgat tggaaagagt tttacagcac cgacaacaaa    180
tatgacgcgc aggctacag cgttgataat gaaaatccgc tgagcggtaa ggctggcggc     240
gtcgttaagg ttacctatcc gggtctgacg aaagtgctgg ccctgaaagt tgacaatgct    300
gaaaccatca aaaagaact gggtctgagc ttgaccgagc cgctgatgga acaggttggt     360
actgaagaat tcattaaacg ttttggtgac ggcgcgagcc gtgttgtgct gtccctgccg    420
tttgccgagg ttctagctc cgtggagtat atcaacaatt gggaacaggc gaaagcgttg     480
agcgtcgagc tggaaatcaa tttcgagact cgtggtaagc gtggccaaga tgcgatgtac    540
gagtacatgg cccaggcatg tgcgggtaac cgcgtccgtc gcagcgtcgg cagctccctg    600
agctgcatta acctggactg ggacgtgatc cgcgacaaga ctaagaccaa gattgagagc    660
ctgaaagagc acggtccgat taagaacaaa atgtccgagt ctccgaacaa acgggtgagc    720
gaagaaaaag ccaaacagta tctggaagaa ttccatcaga ccgccctgga gcacccagag    780
ctgagcgagc tgaaaaccgt caccggcacg aatccggttt tgcgggtgc gaactacgcg     840 gcatgggcag tcaatgttgc gcaagtcatc gacagcgaaa cggctgataa cttggagaaa    900
accaccgcgg cactgagcat tctgccgggc atcggtagcg ttatgggcat tgcggacggt    960
gccgtgcatc acaataccga agaaattgtc gcgcagagca tcgcattgtc tagcctgatg   1020
gttgcacagg ccattccgct ggtaggcgaa ttggtggata tcggtttcgc ggcttacaat   1080
ttcgttgagt cgatcattaa cctgttcaa gtcgttcaca atagctataa ccgtccggca    1140
tacagcccgg gtcataagac gcaaccgttt ctgcatgatg gctatgccgt gagctggaac   1200
acggtcgagg attcgattat ccgtaccggt tttcagggtg agagcggtca cgacatcaaa   1260
atcaccgcgg agaacacgcc gctgcctatt gcgggcgtcc tgctgccgac gatcccgggc   1320
aaactggacg ttaacaagag caagacccat atcagcgtca acggtcgtaa gattcgcatg   1380
cgttgtcgtg caatcgacgg tgacgtgacg ttctgccgcc caaaaagccc ggtgtacgtg   1440
ggtaacggcg tgcacgcgaa tctgcatgtc gcgttccacc gctcctcaag cgagaaaatc   1500
cacagcaatt aaattagcag cgacagcatt ggtgtgttgg gctaccaaaa gaccgtggat   1560
cacaccaagg ttaatagcaa gctgagcctg ttctttgaga tcaaaagc                1608
```

<210> SEQ ID NO 9
<211> LENGTH: 1608
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
atgggtgccg atgacgtggt tgactcttcc aaaagcttcg tcatggaaaa cttcagctcc      60
tatcacggca ctaaaccggg ttatgtcgac agcatccaga aaggcatcca gaaaccgaaa     120
tctggcactc agggtaacta tgacgacgac tggaaagagt tctactctac cgacaacaaa     180
tacgacgcgg ctggttattc tgtggacaac gaaaacccgc tgtctggtaa agctggtggt     240
gttgttaaag tgacctaccc gggtctgacc aaagttctgg ctctgaaagt ggacaacgcc     300
gaaaccatca aaaagaact gggtctgtct ctgaccgaac cgctgatgga acaggtaggt     360
accgaggaat tcatcaaacg ttttggtgat ggtgcgtccc gtgttgtact gtctctgcca     420
tttgccgaag gttctagctc tgtcgagtac atcaacaact gggagcaggc caaagctctg     480
tctgtggaac tggaaatcaa cttcgagacc cgtggtaaac gtggtcagga cgcaatgtat     540
gaatacatgg cacaggcttg cgcgggtaac cgtgtacgtc gttctgtagg ttcttccctg     600
tcttgcatca acctggactg ggatgtcatc cgtgacaaaa ccaaaaccaa aatcgagtcc     660
ctgaaagagc acggtccgat caaaaacaaa atgagcgaat ctccgaacaa aacggtctct     720
gaggaaaaag cgaaacagta cctggaagaa ttccatcaga ccgccctgga cacccggaa      780
ctgtctgaac tgaaaaccgt taccggtact aacccggttt cgcaggtgc taactacgca     840
gcgtgggcgt taacgtagc ccaggtaatc gattccgaaa ccgcagacaa cctggaaaaa     900
acgactgcgg ctctgtctat tctgccgggt attggtagcg tgatgggtat tgcagatggt     960
gcagttcacc acaacacgga agaaatcgtt gcgcagtcta tcgctctgtc ttctctgatg    1020
gtagcacagg cgatcccgct ggttggtgaa ctggttgaca ttggcttcgc ggcctacaac    1080
ttcgttgaat ccatcatcaa cctgttccag gttgtgcaca actcttacaa ccgtccagct    1140
tactctccgg gtcacaaaac ccagccgttc ctgcacgacg gttatgcggt tcttggaac     1200
accgttgaag acagcatcat ccgtactggt ttccagggtg aatctggcca cgacatcaaa    1260
atcactgctg aaaacacccc gctgccgatc gcaggtgttc tcctgccaac tattccgggt    1320
aaactggacg tgaacaaatc caaaacgcac atctccgtga acggtcgtaa atccgcatg     1380
cgttgtcgtg cgattgatgg tgacgttact ttctgtcgtc cgaaatctcc ggtctacgta    1440
ggtaacggtg tacatgctaa cctccatgta gcgttccacc gttcttcttc cgagaaaatc    1500
cactccaacg agatctctag cgactctatc ggtgttctgg ttaccagaa aaccgttgac    1560
cacaccaaag tgaactccaa actcagcctg ttcttcgaaa tcaaatct                 1608
```

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10

```
gagctctaag aaggagatat acatgggtgc cgatgacgtg gttgactct                  49
```

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 11
gagctcttaa gaaggagata tacatgggtg ccgatgacgt ggttgactct          50

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 12
gagctctaag aaggagatat acaatgggtg ccgatgacgt ggttgactct          50

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 13
gagctctaag aaggagatat acacatgggt gccgatgacg tggttgactc t         51

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 14
gagctctaag aaggagatat accatatatg ggtgccgatg acgtggttga ctct      54

<210> SEQ ID NO 15
<211> LENGTH: 112
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 15
tctagaaata attttgttta actttaagaa ggagatatac atatggctag catgactggt      60
ggacagcaaa tgggtcggga tccgaattcg agctctaaga aggagatata cc             112

<210> SEQ ID NO 16
<211> LENGTH: 73
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 16
tctagaaata attttgttta actttaagaa ggagatatac atatggctag catgactggt      60

```
                                       -continued aaggagatat acc                                                    73

<210> SEQ ID NO 17
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tctagaaata attttgttta actttaagaa ggagatatac atatggctag catgactggt    60
gcgmayccat tcagtgaaga agragsttya ttt                                93
```

EXPRESSION AND PURIFICATION OF CRM197 AND RELATED PROTEINS

REFERENCE TO RELATED APPLICATIONS

This application claims priority to U.S. Provisional Application No. 61/934,377 of the same title filed Jan. 31, 2014, the entirety of which is specifically incorporated by reference.

SEQUENCE LISTING

The instant application contains a Sequence Listing which has been submitted electronically in ASCII format and is hereby incorporated by reference in its entirety. Said ASCII copy, created on Feb. 11, 2015, is named 8164.014.PCT_SL.txt and is 14,566 bytes in size.

BACKGROUND

1. Field of the Invention

The present invention relates to the field of recombinant protein production in bacterial hosts. In particular, the present invention relates to a production process for obtaining high levels of soluble recombinant $CRM_{197}$ protein from $E.$ $coli.$ The invention also relates to purification and characterization methods for $CRM_{197}$ as well as uses of the $CRM_{197}$ produced by the method.

2. Description of the Background

Diphtheria toxin (DT) is a proteinaceous exotoxin synthesized and secreted by pathogenic strains of $Corynebacterium$ $diphtheriae$. These pathogenic strains contain a bacteriophage lysogen that carries the toxin gene. Diphtheria toxin is an ADP-ribosylating enzyme that is secreted as a proenzyme of 535 residues and processed by trypsin-like proteases with release of two fragments (A and B). Fragment A uses NAD as a substrate, catalyzing the cleavage of the N-glycosidic bond between the nicotinamide ring and the N-ribose and mediating the covalent transfer of the ADP-ribose (ADPRT activity) to the modified histidine 715 (diphthamide) of the elongation factor EF-2. This post-translational diphthamide modification inactivates EF-2, halting protein synthesis and resulting in cell death. The A fragment of DT (also named C domain) carries the catalytic active site and is the only fragment of the toxin required for the final step of intoxication. The R domain, carried on the B fragment, mediates binding to receptors on the host cell surface and the T domain, also carried on the B fragment, promotes the pH-dependent transfer of fragment A to the cytoplasm. An Arginine-rich disulfide-linked loop connects fragment A to fragment B (or domain C to domains TR). This inter-chain disulfide bond is the only covalent link between the two fragments after proteolytic cleavage of the chain at position 186. The isolation of various non-toxic and partially toxic immunologically cross-reacting forms of diphtheria toxins (CRMs or cross reacting materials) resulted in discovery of $CRM_{197}$ (Uchida et al., Journal of Biological Chemistry 248, 3845-3850, 1973; see also Giannini et al. Nucleic Acids Res. 1984 May 25; 12(10):4063-9). Preferably, CRMs can be of any size and composition that contain all or a portion of DT. $CRM_{197}$ is a largely enzymatically inactive and nontoxic form of diphtheria toxin that contains a single amino acid substitution G52E. This mutation causes intrinsic flexibility of the active-site loop in front of the NAD-binding site and reduces the ability of $CRM_{197}$ to bind NAD and eliminates toxic properties of DT (Malito et al., Proc Natl Acad Sci USA 109(14):5229-342012) Like DT, $CRM_{197}$ has two disulfide bonds. One disulfide joins Cys186 to Cys201, linking fragment A to fragment B. A second disulfide bridge joins Cys461 to Cys471 within fragment B. Both DT and CRM197 have fragment A-associated nuclease activity (Bruce et al., Proc. Natl. Acad. Sci. USA 87, 2995-8, 1990).

Many antigens are poorly immunogenic, especially in infants, unless chemically linked to a protein ("conjugation"), thereby forming a conjugate or conjugate vaccine. The protein component of these conjugate vaccines is also called the "carrier protein". $CRM_{197}$ is commonly used as the carrier protein for protein-carbohydrate and hapten-protein conjugates. As a carrier protein, $CRM_{197}$ has a number of advantages over diptheria toxoid as well as other toxoid proteins, many of which have been documented (Shinefield Vaccine, 28:4335, 2010, Broker et al, Biologicals, 39:195 2011). For example since $CRM_{197}$ is genetically detoxified, it retains a larger complement of lysines, which are used for conjugation but are blocked by chemical toxoiding. $CRM_{197}$ has proven to be an effective carrier protein for $Streptococcus$ $pneumonia$ capsular polysaccharides, as evidenced by the success of PREVNAR™ (Pfizer), a vaccine consisting of up to 13 capsular polysaccharides chemically linked to $CRM_{197}$. There is also evidence suggesting that compared with tetanus toxoid, there is less carrier-induced suppression of the immune response, especially when there are many individual polysaccharides linked to the same carrier protein.

$CRM_{197}$ and native DT have a similar affinity for the diphtheria toxin receptor (DTR), which has an identical amino acid sequence to the HB-EGF precursor pro-HB-EGF (Mitamura et al., J. Biol. Chem. 272(43):27084-90, 1997). $CRM_{197}$ binds to the soluble form of HB-EGF, as well as to the membrane form pro-HB-EGF, and inhibits HB-EGF mitotic action by preventing its binding to EGF receptor. Thus $CRM_{197}$ may also have a future role in cancer therapy (Miyamoto et al., Anticancer Res. November-December 27(6A):3713-21, 2007).

$CRM_{197}$ has been produced in the original host $Corynebacterium$, but yields are low, typically <50 mg/L and, in addition, $Corynebacterium$ growth is relatively slow as compared with, for example, $E.$ $coli$. There are proprietary strains of $Corynebacterium$ that have been engineered to produce $CRM_{197}$ at higher levels (U.S. Pat. No. 5,614,382). $CRM_{197}$ has also been expressed in a proprietary strain of $Psuedomonas$ $fluorescens$ and expressed at high levels. Production of $CRM_{197}$ in $E.$ $coli$ would be advantageous since $E.$ $coli$ is a BL1 level organism that is inexpensive to culture and propagate. Production of $CRM_{197}$ in $E.$ $coli$ has mainly resulted in insoluble inclusion bodies (generally insoluble), which then requires a difficult refolding process, resulting in low yields (EP20100742260) or with an additional peptide sequence (a tag) (J Biotechnol. 2010 December 20; 156(4):245-52, Overexpression and purification of the recombinant diphtheria toxin variant CRM197 in $Escherichia$ $coli$. Stefan A, Conti M, Rubboli D, Ravagli L, Presta E, Hochkoeppler A. A method for the overexpression of soluble tag free $CRM_{197}$ in $E.$ $coli$ suitable for the large quantity protein production, has not been reported. Thus, there is a need for better methods to produce $CRM_{197}$ in an efficient and cost-effective manner.

SUMMARY OF THE INVENTION

The present invention overcomes the problems and disadvantages associated with current strategies and designs and provide new compositions and methods for producing CRM.

One embodiment of the invention is directed to methods of producing all or a portion of a CRM protein comprising: providing a recombinant cell that contains an expression vector that contains an inducible promoter functionally linked to a polycistronic genetic sequence wherein at least one cistron encodes the CRM protein; inducing the expression vector to produce CRM protein; and isolating the CRM protein expressed. Preferably the recombinant cell has a reduced activity of one or more disulfide reductase enzymes and also preferably, each cistron contains a ribosome binding site and an initiation codon. Preferably the polycistronic genetic sequence contains at least one spacer between one or more ribosome binding sites and one or more initiation codons. Preferably the CRM protein expressed by the cell is soluble and also preferably, the CRM protein expressed is intracellular, periplasmic or secreted. Preferably the recombinant cell is propagated at a temperature from about 15° C. to about 32° C. and also preferably, the CRM protein is isolated from the cell by chromatography. Preferable chromatography media include, for example, a dextran sulfate resin, a gel resin, an active sulfated resin, a phosphate resin, a heparin resin or a heparin-like resin. Another embodiment of the invention comprises CRM protein isolated by the methods of the invention.

Another embodiment of the invention is directed to methods of producing all or a portion of a CRM protein, such as preferably $CRM_{197}$. comprising; providing a recombinant cell that contains an expression vector, wherein the recombinant cell has been modified to shift the redox status of the cytoplasm to a more oxidative state as compared to an unmodified recombinant cell and the expression vector contains an inducible promoter functionally linked to a CRM coding sequence, a spacer sequence between a ribosome binding site and an ATG codon, an expression enhancer region upstream of the CRM coding sequence; inducing the expression vector to produce CRM protein; and isolating the CRM protein expressed. The recombinant cell may be a eukaryotic cell or a prokaryotic cell. Preferably the recombinant cell is a prokaryotic cells such as, for example, an E. coli cell or a derivative or strain of E. coli. Preferably, the recombinant cell modification comprises a reduced activity of one or more disulfide reductase enzymes such as, for example, one or more of an oxidoreductase, a dihydrofolate reductase, a thioredoxin and thioredoxin reductase, a protein reductase or a glutathione reductase. Preferably the reduced activity of the one or more disulfide reductase enzymes shifts the redox state of the cytoplasm of the recombinant cell to an oxidative state as compared with a non-recombinant cell. Preferably the CRM coding sequence encodes one or more CRM epitopes, CRM peptide sequences, CRM domains, or combinations thereof. Preferably the spacer comprises more or less than 9 nucleotides such as, for example, between 5 and 20 nucleotides. Preferably the expression enhancer comprises a ribosome binding site upstream of the CRM coding sequence and an ATG codon. Preferably the CRM protein expressed by the cell is soluble and is intracellular, periplasmic or secreted. Preferably the recombinant cell is propagated at a temperature from about 15° C. to about 32° C.

Preferably, the CRM protein is isolated from the cell by chromatography comprising, as a preferable chromatography medium, a dextran sulfate resin, an active sulfate resin, a phosphate resin, a heparin resin or a heparin-like resin.

Another embodiment of the invention is directed to CRM protein isolated by the methods of the invention. Preferably, the isolated CRM protein is conjugated and the conjugated CRM protein is formulated as a vaccine.

Another embodiment of the invention is directed to methods of producing all or a portion of a CRM protein such as for example a protein or peptide produced from a CRM coding sequence that encodes one or more CRM epitopes, CRM peptide sequences, CRM domains, or combinations thereof, and preferably $CRM_{197}$, comprising providing a recombinant cell that contains an expression vector, wherein the expression vector contains a promoter functionally linked to an EES coding sequence preceded by a ribosome binding site; expressing CRM protein from the CRM coding sequence preceded by a ribosome binding site; and isolating the CRM protein expressed. Preferably the recombinant cell is a prokaryotic or a eukaryotic cell and preferably the prokaryotic cell is an E. coli cell or a derivative or strain of E. coli. Preferably the promoter is constitutive or inducible. Preferably the recombinant cell has been modified to shift the redox status of the cytoplasm to a more oxidative state as compared to an unmodified recombinant cell. Preferably the modified recombinant cell has reduced activity of one or more of an thiol-disulfide oxidoreductases, and or enzymes involved in the thioredoxin and glutaredoxin systems (e.g. thioredoxin, thioredoxin reductase, glutathione reductase) Preferably the expression vector contains controlled by ribosome binding site an expression enhancer sequence (e.g., SEQ ID 15) or such as, for example including T7 tag sequence, upstream ribosome binding site upstream of the CRM coding sequence.

Another embodiment of the invention is directed to methods for isolating and/or purifying CRM protein comprising: loading the CRM protein onto a chromatography column containing a resin with a loading buffer wherein the resin is preferably a dextran sulfate resin, a, an active sulfate resin, a phosphate resin, a heparin resin or a heparin-like resin; washing the resin with one or more washing buffers; and eluting CRM protein from the resin with an elution buffer. Preferably the loading buffer and the washing buffer are or contain the same components and at the same or in similar amounts. Preferably the loading buffer and the one or more washing buffers are low conductivity buffers such as, for example, Tris-HCl, HEPES, sodium phosphate buffers a conductivity of about 10 mS/cm or less (e.g., 1 mS/cm, 2 mS/cm, 3 mS/cm, 4 mS/cm, 5 mS/cm, 6 mS/cm, 7 mS/cm, 8 mS/cm, 9 mS/cm). Preferably the elution buffer is a high conductivity buffer such as, for example, buffers with added salts such for example, NaCl, or KCl, at a conductivity of about 10 mS/cm or more (e.g., 12 mS/cm, 14 mS/cm, 15 mS/cm, 20 mS/cm, 25 mS/cm, 30 mS/cm, 40 mS/cm, 50 mS/cm, 60 mS/cm, 70 mS/cm, 80 mS/cm, 90 mS/cm, 100 mS/cm or more).

Another embodiment of the invention is directed to methods of characterizing folding of diphtheria toxin or CRM protein comprising: contacting diphtheria toxin or CRM protein to HB-EGF; determining the amount of binding of diphtheria toxin or CRM protein to HB-EGF; and determining the folding of diphtheria toxin or CRM protein by the amount of binding determined, wherein binding indicates correct folding. Preferably the diphtheria toxin or CRM contains a receptor binding domain. Preferably the CRM protein comprises $CRM_{197}$. Also preferably the at least one of the diphtheria toxin or CRM protein and/or the HB-EGF is bound to a solid support. Preferably the amount of binding of diphtheria toxin or CRM protein to HB-EGF is determined by an ELISA and the CRM protein that binds to HB-EGF is soluable in PBS.

Another embodiment of the invention comprises expression vectors that comprise a promoter and two or more cistrons at least one encoding a protein, wherein at least one cistron encodes CRM protein and each cistron has a ribosome binding site and an initiation codon. Preferably the expression vector further comprising a spacer between the ribosome binding site and the initiation codon and also preferably the spacer comprises from 5 to 20 nucleotides. Preferably the spacer does not comprise 9 nucleotides.

Other embodiments and advantages of the invention are set forth in part in the description, which follows, and in part, may be obvious from this description, or may be learned from the practice of the invention.

DESCRIPTION OF THE DRAWINGS

FIG. 1 Schematic of vector constructs crm7 (SEQ ID NO 10), crm7_2 (SEQ ID NO 11), crm 8 (SEQ ID NO 12), crm 9 (SEQ ID NO 13), and crm 12 (SEQ ID NO 14) with the ribosome binding site (RBS) and start codon (ATG) both indicated in bold with the spacer sequence underlined.

FIG. 2 Results of titration of mouse anti-pn6B sera on immunotech plates coated with 2 μg/ml of pn6B.

FIG. 3 Results of titration of anti-pn14 sera on pn14 coated plates.

DESCRIPTION OF THE INVENTION

Soluble, intact recombinant CRM was first produced in protease-deficient *E. coli* (Bishai et. al 1987). However, the amount of protein production was very low. Subsequently, $CRM_{197}$ was produced in *E. coli* cells as inclusion bodies (Stefan A, et al. J Biotechnol. December 20; 156(4):245-52, 2010; International Application Publication No. WO 2011/126811, Chinese Patent Application No. 200610042194) or as soluble protein directed to the periplasm by signal peptide (International Application Publication No. WO 2011/042516). The periplasm of *E. coli* is an oxidizing environment that allows the formation of disulfide bonds. $CRM_{197}$ has two disulfide bonds that are probably important for the correct folding and function, and for protein solubility.

It has been surprisingly discovered that a single, uncleaved chain of soluble recombinant CRM protein can be rapidly produced intracellularly and in commercial quantities from microorganisms and thereafter isolated and/or purified in large quantities and remain soluble. CRM is soluble in phosphate buffered saline (PBS, pH 7.5) and other similar buffers and can be concentrated to greater than 5 mg/ml in this and other buffers while remaining soluble. While CRM expressed in Cornybacter can be concentrated in these buffers, CRM made in *Pseudomonas* and expressed in the periplasm, cannot be easily concentrated in these same buffers (Pfenex Inc., San Diego, Calif.). A further advantage of intracellular expression compared with periplasmic expression is that greater expression levels are achieved because the periplasmic space is limiting compared to intracellular space.

Preferred CRM proteins produced are full length or partial regions such as, for example, peptides, single or multiple domains or epitopes, and any specific region expressed from native CRM coding sequences including CRM sequences that have been modified with one or more deletions, substitution and/or additions (e.g. conservative or non-conservative), and CRM sequences that have been modified with additional sequences (e.g., one or more promoters, start codons, and translation factor, ribosome or polymerase binding sites) that promote expression in a host organism. A preferred CRM protein is $CRM_{197}$. Preferred is expression of CRM protein that is soluble and not otherwise bound as insoluble inclusion bodies of the cell. Preferred expression systems for the expression and production of CRM proteins include microorganisms with an intracellular oxidative state. Preferred expression systems may be recombinant or native eukaryotic or prokaryotic cells wherein recombinant cells include cells that contain a non-native CRM coding sequence. Preferred prokaryotic cells are strains of *E. coli* or another bacterial strain that contains one or more genetic alterations (e.g., one or more deletions or mutations). Preferably the one or more genetic alterations shift the redox state of the cytoplasm of the cell to a more oxidative state, as compared to wild-type, for example as disclosed in U.S. Pat. No. 7,410,788 (which is incorporated by reference). Alterations preferably reduce the activity of one or more disulfide reductase genes and/or other genes that reduce the oxidative state of the cytoplasm. Preferably, reduced activity is due to non-expression or reduced expression of one, two or multiple disulfide reductase or other genes, or one or more mutations that reduce activity of one or more expressed disulfide reductase proteins or other proteins. Preferred strains of microbial cells (e.g., recombinant, engineered or native eukaryotic or prokaryotic cells) have increased abilities to produce natively folded proteins containing disulfide bonds yet remain as functional proteins. The method of the invention produces quantities of CRM proteins containing full, truncated or modified CRM amino acid sequences. Quantities of CRM protein produced according to the invention are surprising such as, for example, 600 mg or more of CRM protein per liter of bacterial cell culture.

One embodiment of the invention is directed to methods for the production of large quantities of CRM protein, and preferably $CRM_{197}$. Production quantities are typically quantified as mg/L of bacterial cell culture. CRM protein production, according to the methods of the invention, is 200 mg/L or more, 300 mg/L or more, 400 mg/L or more, 500 mg/L or more, 600 mg/L or more, 700 mg/L or more, 800 mg/L or more, 900 mg/L or more, 1,000 mg/L or more, 1,500 mg/L or more, or 2,000 mg/L or more. Preferred quantities $CRM_{197}$ of the invention includes related proteins containing full length and truncated CRM protein, as well as modified amino acid sequences of CRM protein. Modifications include one or more of conservative amino acid deletions, substitution and/or additions. A conservative modification is one that maintains the functional activity and/or immunogenicity of the molecule, although the activity and/or immunogenicity may be increased or decreased. Examples of conservative modifications of CRM include, but are not limited to amino acid modifications (e.g., single, double and otherwise short amino acid additions, deletions and/or substitutions), modifications outside of the 39 alpha-amino groups of lysine (primary amine groups of lysine) residues that are accessible for conjugation in forming a vaccine, modifications due to serotype variations of DT, modifications that increase immunogenicity or increase conjugation efficiency, modification that do not substantially alter binding to heparin, modifications that maintain proper folding or three dimensional structure, and/or modifications that do not significantly alter immunogenicity of the protein or the portions of the protein that provide protective immunity to DT.

Recombinant cells that are used in the method of the invention are preferably *E. coli* bacteria and, preferably, *E. coli* that are genetically engineered to shift the redox state of the cytoplasm to a more oxidative state such as, for example, by mutation of one or more disulfide reductase genes such as, for example, an oxidoreductase, a dihydrofolate reductase, a thioredoxin reductase, a glutamate cysteine lyase, a disulfide reductase, a protein reductase, and/or a glutathione reductase. Preferably one or more disulfide reductase genes are mutated and rendered non-functional or marginally functional such that the redox state of the cytoplasm of the cell is shifted to a more oxidative state as compared to wild type. Oxidative protein folding involves the formation and isomerization of disulfide bridges and plays a key role in the stability and solubility of many proteins including $CRM_{197}$. Formation and the breakage of disulfide bridges is generally catalyzed by thiol-disulfide oxidoreductases. These enzymes are characterized by one or more Trx folds that consist of a four-stranded β-sheet surrounded by three α-helices, with a CXXC redox active-site motif. The assembly of various Trx modules has been used to build the different thiol oxidoreductases found in prokaryotic and in eukaryotic organisms. In the bacterial periplasm, the proteins are kept in the appropriate oxidation state by a combined action of the couples DsbB-DsbA and DsbD-DsbC/DsbE/DsbG (Inaba 2009, Gruber et al, 2006). Many protein expression systems are well known in the art and commercially available.

Especially preferred microbes include *E. coli* expression strains, for example, chemically competent *E. coli* K12 cells engineered to form disulfide bonded proteins in the cytoplasm (e.g., ORIGAMI™ (EMD Millipore) and SHUFFLE™ (New England Biolabs)). Other strains and types of cells and other *E. coli* strains with enhanced oxidative redox state also may be used. For example, ORIGAMI™ 2 host strains are K-12 derivatives that have mutations in both the thioredoxin reductase (trxB) and glutathione reductase (gor) genes, which greatly enhance disulfide bond formation in the *E. coli* cytoplasm. These strains are kanamycin sensitive; like the original Origami strains, the gor mutation is still selected for by tetracycline. To reduce the possibility of disulfide bond formation between molecules, strains containing mutations in trxB and gor are recommended only for the expression of proteins that require disulfide bond formation for proper folding. SHUFFLE™ cells are chemically competent *E. coli* K12 cells engineered to form proteins containing disulfide bonds in the cytoplasm. Preferably these cells contain mutations in trxB and gor and cytoplasmic chaperon disulfide bond isomerase DsbC (fhuA2 [lon] ompT ahpC gal λatt::pNEB3-r1-cDsbC (SpecR, lacI$^q$) ΔtrxB sulA11 R(mcr-73::miniTn10—Tet$^S$)2 [dcm] R(zgb-210::Tn10—Tet$^S$) endA1 Δgor Δ(mcrC-mrr)114::IS10). Also preferably, cells are suitable for T7 promoter driven protein expression and of the genotype F' lac, pro, lacIQ/Δ(ara-leu)7697 araD139 fhuA2 lacZ::T7 gene1 Δ(phoA)PvuII phoR ahpC* galE (or U) galK λatt:pNEB3-r1-cDsbC (Spec$^R$, lacI$^q$) ΔtrxB rpsL150(Str$^R$) Δgor Δ(malF)3. SHUFFLE™ strains expresses constitutively a chromosomal copy of the disulfide bond isomerase DsbC. DsbC promotes the correction of mis-oxidized proteins into their correct form. Cytoplasmic DsbC is also a chaperone that can assist in the folding of proteins that do not require disulfide bonds.

Bacterial cultures are preferably cultured at temperatures such that solubility of the expressed protein increases (e.g., CRM or $CRM_{197}$) as compared to solubility at higher temperatures (e.g., 37° C.). Preferred culture temperatures are 30° C. or lower, preferably 25° C. or lower, preferably 20° C. or lower, preferably 18° C. or lower, and preferably between 15° C. and 32° C.

Another embodiment of the invention is directed to vectors for producing CRM and methods of producing all or a portion of a CRM protein, such as preferably $CRM_{197}$, soluble in the cytoplasm of a cell and preferably a prokaryotic cell. Previous attempts to express CRM in *E. coli* intracellularly were based on monocystronic mRNA, encoding only the CRM sequence and resulted in inclusion body formation. Methods of producing soluble CRM in the cytoplasm of cells were developed using an expression vector that provides transcription of CRM in polycistronic mRNA. Polycistronic mRNA refers to messenger RNA that encodes two or more polypeptides. In prokaryotic cell, genes that are involved in the same biochemical or physiological pathway are often grouped into an operon, controlling transcription of the genes into a single polycistronic mRNA. Genes (cistrons) in the operon are controlled by a ribosome binding site sequences and can be separated by a number of nucleotides or even overlapping sequences, For example, a stop codon of the first gene is downstream of the second gene start codon, as in the galactose operon. Gene location in the operon has been shown to also strongly affect gene expression level via translational and mRNA stability effects (Smolke, C. D., and Keasling, J. D. (2002) Effect of gene location, mRNA secondary structures, and RNase sites on expression of two genes in an engineered operon. Biotechnol. Bioeng. 80, 762-76). The downstream gene expression level is found to be enhanced by the upstream gene expression via translational coupling (Schumperli, D., McKenney, K., Sobieski, D. a, and Rosenberg, M. (1982) Translational coupling at an intercistronic boundary of the *Escherichia coli* galactose operon. Cell 30, 865-71). One preferred embodiment of the invention is a vector comprising a prokaryotic promoter and two cistrons encoding polypeptides, one of them being CRM. Each cistron comprises a ribosome binding site and an initiation codon such as, for example, ATG. The invention further includes inducing the expression vector to produce CRM protein and isolating the CRM protein expressed. In one preferred embodiment, the first cistron preceding the CRM sequence contains the T7 tag sequence, overlapping with the CRM cistron, so that stop codon for the first cistron is downstream of the initiation codon of CRM (e.g. SEQ ID NO 15). The expression enhancer is further modified as SEQ ID NO 16 or SEQ ID NO 17. The first cistron preceding CRM coding sequence is termed an "expression enhancer sequence" (EES). The expression vector contains (1) a promoter followed by a ribosome binding site and the expression enhancer sequence, and (2) a ribosome binding site and an ATG codon and the CRM coding sequence. The recombinant cell may be a prokaryotic or eukaryotoc cell. Preferably the recombinant cell is a prokaryotic cell such as, for example, an *E. coli* cell or a derivative or strain of *E. coli*. Preferably, the recombinant cell modification comprises a reduced activity of one or more disulfide reductase enzymes such as, for example, one or more of an oxidoreductase, a dihydrofolate reductase, a thioredoxin and a thioredoxin reductase, a protein reductase or a glutathione reductase. Preferably the reduced activity of the one or more disulfide reductase enzymes shifts the redox state of the cytoplasm of the recombinant cell to an oxidative state as compared with a non-recombinant cell. Preferably the CRM coding sequence encodes one or more CRM epitopes, CRM peptide sequences, CRM domains, or combinations thereof. Preferably the CRM protein expressed by the cell is soluble and is intracellular, periplasmic or secreted. Preferably the recombinant cell is propagated at a temperature from about 15° C. to about 32° C.

Another embodiment of the invention comprises recombinant cells such as, for example, bacterial, mammalian or insect cells containing expressible CRM sequences and, preferably sequences of $CRM_{197}$. Preferred host cells include, but are not limited to, cells genetically engineered to shift the redox state of the cytoplasm to a more oxidative state. Preferred cells include prokaryotic or eukaryotic cells such as, for example, *E. coli* cell expression systems, Baculovirus Expression System and other bacterial and/or eukaryotic cellular expression systems. Preferably the cells contain a protein expression system for expressing foreign or non-native sequences such as CRM peptides. Also preferable, the sequences to be expressed are comprised of an expression vector which contains one or more of an inducible promoter (e.g., auto-inducible preferably with specific media), a start codon (e.g., ATG), a ribosome binding site, unspecified polypeptide sequence and CRM coding sequence transcribed into polycistronic mRNA. Also preferably, the expression vector contains a modified sequence between ribosome binding site and ATG starting codon, or between start codon and the sequence to be expressed. Preferred modified sequences or spacer sequences include, for example, a number of nucleotides more or less than 9 (e.g., between 7 and 12 nucleotides), and preferably not 9 nucleotides. Specific examples of spacer nucleotides that can be utilized in an expression system include but are not limited to GATATAC (SEQ ID NO 3), GATATACCA (SEQ ID NO 4), and GATATACCATAT (SEQ ID NO 5). Accordingly, another embodiment of the invention comprises an expression construction of CRM, nucleotide and amino acids sequences, with or without defined spacer sequences and with and without a host cell.

Another embodiment of the invention is directed to recombinant $CRM_{197}$ protein and the expression of recombinant CRM in *E. coli* or another host cell using an expression vector with an inducible promoter and/or a modified sequence between ribosome binding site and ATG starting codon. Preferably, the expression vector includes the lactose/IPTG inducible promoter, preferably a tac promoter, and the sequence between ribosome binding site and ATG starting codon. Preferably the expression system contains a spacer between the start codon and the expression sequence which is comprised of a number of nucleotides more or less than 9 (e.g., between 7 and 12 nucleotides), and preferably not 9 nucleotides. Specific examples of spacer nucleotides that can be utilized in an expression system include but is not limited to those identified herein. It was surprisingly discovered that the use of spacers of length seven or twelve resulted in dramatically increased levels of $CRM_{197}$ expression when compared to spacers of nine nucleotides.

Another embodiment of the invention comprises an expression construction of CRM, nucleotide and amino acids sequences, with or without defined spacer sequences, as disclosed herein, and with or without an enhancer region. Enhancers regions promote expression of the downstream CRM sequence by translational coupling enhancing correct folding of CRM resulting in protein solubility. Enhancers regions also promote protein expression by adding one or more sequences that promote nucleic acid recognition for increased expression (e.g., start codon, enzyme binding site, translation or transcription factor binding site). Preferably, an enhancer of the invention contain a ribosome binding site with a start codon upstream of and with a coding sequence that differs from the coding sequence of the CRM protein.

Another embodiment of the invention is directed to recombinant CRM, and in particular $CRM_{197}$, purified according to the methods of invention. Purification preferably comprises heparin or heparin-like affinity chromatography. It was surprisingly discovered that $CRM_{197}$ contains the sequence-based motif of typical heparin binding sites XBBXBX (SEQ ID NO 6) where B is a lysine or arginine and X a hydropathic residue (Cardin A D, Weintraub H J., 1989: Molecular modeling of protein-glycosaminoglycan interactions. Arteriosclerosis 9: 21-32). This motif is located in the $CRM_{197}$ receptor-binding domain and comprises of the following amino acids: GRKIRMRCR (SEQ ID NO 7), where G (Glycine), I (Isoleucine), M (Methionine) and C (Cysteine) are hydropathic residues. Presence of heparin binding site allows the use of heparin or heparin-like resins in the purification. Heparin-like resins include resins containing functional sulfate groups, such as dextran sulfate, e.g. Dextran sulfate (Sterogene), Capto Devirs (GE) or sulfate esters, e.g. Cellufine Sulfate (Asahi Kasei Bioprocess).

In a first step, crude *E. coli* extract may be clarified, for example, preferably by centrifugation or depth filtration. Optionally cleared lysate may be fractionated further, preferably by adding salts that have effect on protein solubility and salting out $CRM_{197}$. In the second step, clarified lysate or re-solubilized salted out fraction containing $CRM_{197}$ may be applied, for example, to anion exchange resin under conditions when $CRM_{197}$ is in flow through. In the third step, the flow through fraction containing $CRM_{197}$ may be applied to a column. Preferred column resins include, but are not limited to dextran sulfate resins, CELLUFINE™ resins (Chisso Corporation; chromatography gel), active sulfated resins, phosphate resins, or heparin or heparin-like resins. Preferably binding of CRM to resin is performed in a low salt buffer and eluted in higher salt buffer, yielding highly purified $CRM_{197}$. Preferred binding buffers contain, for example, one or more chaotropic agents, NaCl, KCl, glycerol, isopropyl alcohol, ethanol, arginine, acetate, guanidine, urea, ATP, one or more mono-, di-, tri-, and/or poly-phosphates, sulfates or pyrophosphates, and combinations thereof. Preferred elution buffers contain, for example, higher concentration of one or more components of the binding buffer.

Other preferred purification methods include any one or combination of an anion exchange chromatography, hydrophobic interaction chromatography and/or Cibacron-Blue resin (CN 101265288A, U.S. Pat. No. 8,383,783). Purification method of the invention produce recombinant CRM protein (e.g., $CRM_{197}$) at high yields, as discussed herein, and with a purity level of greater than 80%, preferably greater than 85%, preferably greater than 90%, preferably greater than 95%, preferably greater than 99%, and preferably with an even greater purity.

Another embodiment of the invention is directed to methods to characterize recombinant DT and CRM proteins (e.g., binding activity) and, in particular $CRM_{197}$, which contain a receptor binding domain (see SEQ ID NO 2). These methods comprise determination of the binding activity of proteins containing native or modified sequence of receptor binding domain of DT. Such modifications preferably preserve the ability of CRM to bind to HB-EGF (heparin binding epidermal growth factor). The method is applicable to both crude and purified $CRM_{197}$. Binding activity represents binding to the soluble form of diphtheria toxin receptor HB-EGF (DTR). These methods comprise, preferably, determining the binding $CRM_{197}$ to DTR and detection of with molecules (e.g., antibodies, antibody fragments, antigens) specific to the properly folded structure, the complex, binding, and/or the binding sites, and preferably in an ELISA format. Assays to determine and quantitate binding allow for the rapid determination that $CRM_{197}$ is correctly folded, as only properly folded $CRM_{197}$ binds to the receptor. Thus, the method monitors correct folding of manufactured $CRM_{197}$ and related proteins during the development, production and purification process. In addition, this characterization method can be used to identify and track CRM protein after conjugation with another molecule such as in vaccine production. Using the detection method of the invention, properly folded and configured conjugated CRM protein can be monitored during the development of a vaccine for the treatment and/or prevention of diseases and disorders in patients.

Another embodiment of the invention comprises methods for conjugating CRM protein for vaccine production, such as, for example, by conjugation with a polysaccharide. Also included are the conjugation of proteins, peptides oligosaccharides and haptens. Another embodiment of the invention comprises a vaccine containing CRM protein of the invention. Another embodiment of the invention is directed to CRM protein of the invention fused genetically or chemically with another molecule, such as another protein or polysaccharide. Fusion is preferably by one or more covalent bonds between the molecules.

The following examples illustrate embodiments of the invention, but should not be viewed as limiting the scope of the invention.

EXAMPLES

Example 1. $CRM_{197}$ Expression Detected from Expression Vectors Containing 7, 8, 9 or 12 Nucleotides Sequence Between RBS and Initial ATG Codon DNA encoded mature $CRM_{197}$ was cloned into expression vector in polycistronic format resulting in the following sequence of DNA regulatory and coding fragments: tac promoter-ribosome binding site-ATG codon-T7 tag-ribosome binding site-ATG codon-CRM coding sequence-stop codon. Different *E coli* strains, including ORIGAMI 2, C41, were tested as expression strains (FIG. 1).

Example 2. $CRM_{197}$ Expresses Soluble in Origami 2, *E. coli* Expression Strain that Allows Formation of Disulfide Bonds in the Cytoplasm $CRM_{197}$ was expressed insoluble at 37° C. When expression temperature was dropped below 37°, solubility of the protein expressed in ORIGAMI™ 2 cells and SHUFFLE™ cells, but not in the other tested *E. coli* strains, increases. $CRM_{197}$ is mostly soluble when expressed in ORIGAMI™ 2 cells at 18° C.

Example 3. Expression Enhancer Sequence (EES) in $CRM_{197}$ Expression

The EES promotes transcription of CRM sequence in a CRM-containing vector and results in polycistronic mRNA that translates into two proteins; a short EES peptide and a CRM peptide. The coding sequence of the native CRM gene was analyzed for potential 3D structure formation and found to contain a number of potential hairpins, which could inhibit translation. A CRM sequence was created that would potentially result in an mRNA with no hairpins structures yet translate the same CRM amino acid sequence. This gene sequence is referred to an optimized CRM sequence and comprises SEQ ID NO 8.

The optimized CRM sequence expresses well in both *E. coli* (e.g., BL21) and in *E. coli* engineered to contain an oxidized cytoplasm (e.g., Shuffle). CRM peptide translated from polycistronic mRNA produces a full length protein and is believed to be more stable than the native CRM coding sequence. Unlike the native CRM sequence, the optimized CRM sequence expressed as full-length and as a soluble protein in Shuffle cells. In addition, compared to native CRM, higher expression of the optimized CRM sequence is observed with a lower cell density and with increased binding to chromatography resin resulting in greater production levels of CRM protein.

Example 4. Ammonium Sulfate Precipitation of $CRM_{197}$ from Cell Lysate

SHUFFLE™ cells expressing $CRM_{197}$ were open using microfluidizer and 1M of sodium chloride was added to the cell lysate. To this was added enough ammonium sulfate to equal 1M followed by centrifugation for 30 minutes at 20,000×g, which removed mis-folded $CRM_{197}$ and most of the bacterial proteins. Following clarification the ammonium sulfate concentration was further increased to 2.2M. The precipitate, which is mainly $CRM_{197}$ was collected and re-solubilized in a low conductivity buffer.

Example 5. Purification of $CRM_{197}$ on a Heparin Column

Ammonium sulfate precipitated $CRM_{197}$ was resolubilized in 20 mM Tris-HCl pH 8.0 to achieve conductivity 5 mS/cm and loaded on an column containing Heparin Sepharose CL-6B resin (GE). The purification was performed under the following conditions: flow rate was 5 ml/min, wash buffer A: 20 mM Tris-HCl pH8. Elution was done with a buffer B 0-100% gradient, buffer B: buffer A+1M NaCl in 20 CV. Eluted $CRM_{197}$ was analyzed by SDS-PAGE in reduced and non-reduced conditions. The purity of eluted $CRM_{197}$ was greater than 95%. The protein reduced with DTT appears as a single polypeptide confirming that the intact form of $CRM_{197}$ is expressed in *E. coli.*

Example 6. Purification of $CRM_{197}$ on Capto Devirs Column

SHUFFLE™ cells expressing $CRM_{197}$ were opened using a microfluidizer in 1×PBS, pH 7.4, 1% sodium pyrophosphate. The lysate was clarified using depth filtration. Clarified lysate was loaded on a column containing Q Sepharose XL (GE) and flow through fraction was collected. To reduce volume and conductivity flow through fraction was subjected to tangential flow filtration using 10K cassette (Sartorius). Capto Devirs resin was equilibrated with 25 mM sodium phosphate buffer, pH8.0. $CRM_{197}$ was bound to the column under the following conditions: conductivity was less than 10 mS/cm, in a binding buffer containing a chaotropic agent (e.g., in this case urea), wash buffer was 25 mM sodium phosphate, pH8.0. Elution was done with NaCl. Eluted $CRM_{197}$ was analyzed by SDS-PAGE under reduced and non-reduced conditions. The purity of eluted $CRM_{197}$ was greater than 95%. The protein, reduced with DTT, appears as a single polypeptide confirming that $CRM_{197}$ remains intact during purification process.

Example 7. Binding Assay for the $CRM_{197}$ Characterization

The recombinant soluble diphtheria toxin receptor HB-EGF (DTR) (Sigma) was bound to the ELISA plate. Blocking solution of 5% dry non-fat milk was used to prevent high background. Recombinant $CRM_{197}$ diluted in 1×PBS, pH7.4, 0.1% Twin 20 was incubated on the plate for 1 hour at 37° C. $CRM_{197}$ bound to HB-EGF was detected by rabbit polyclonal anti-$CRM_{197}$ antibody and goat anti-rabbit antibody conjugated to soybean peroxidase (Fina BioSolutions; Rockville, Md.). Denatured recombinant $CRM_{197}$ did not bind to the receptor.

Example 8. $CRM_{197}$ Produced in *E. coli* Binds to DTR Similarly to CRM from *Corynebacterium* and *Pseudomonas*

ELISA plates were coated with soluble HB-EGF (heparin-binding EGF-like growth factor) and blocked with 5% dry non-fat milk. $CRM_{197}$ was bound to the receptor and detected with rabbit anti-$CRM_{197}$ polyclonal antibody and goat anti-rabbit polyclonal conjugated with SBP. $CRM_{197}$ expressed in *E. coli* showed the same affinity to HB-EGF as CRM produced in *Corynebacterium* and *Pseudomonas*.

Example 9. $CRM_{197}$ is a Carrier Protein $CRM_{197}$, was expressed and purified according to the method of this invention (Example 1) and chemically linked (conjugated) to pneumococcal capsule polysaccharides serotypes 14 and 6B using CDAP chemistry (Lees, A., Producing immunogenic constructs using soluble carbohydrates activated via organic cyanylating reagents. See U.S. Pat. Nos. 5,651,971; 5,693,326 and 5,849,301). The conjugates were purified from unconjugated protein and polysaccharide. BALB/c female mice were immunized subcutaneously with the conjugate according to the schedule in Table 1. Mice were immunized in complete Freund's adjuvant and boosted twice in incomplete Freund's adjuvant and day 57 bleeds were taken.

TABLE 1

| Serotype | Primary in CFA* | Boost IFA** | Boost IFA** | D57 |
|---|---|---|---|---|
| 6B | 20 ug | 10 ug day 28 | 10 ug day 48 | bleed |
| 14 | 20 ug | 5 ug day 21 | 5 ug day 48 | bleed |

*60% Complete Freund's Adjuvant;
**60% Incomplete Freund's Adjuvant

Figure 2:
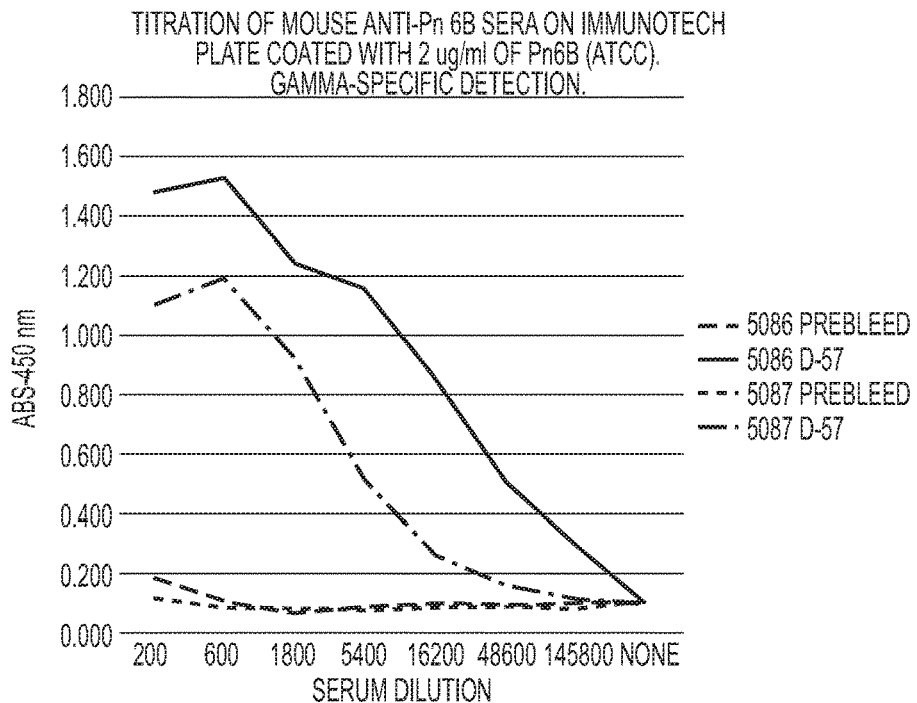
Figure 3:
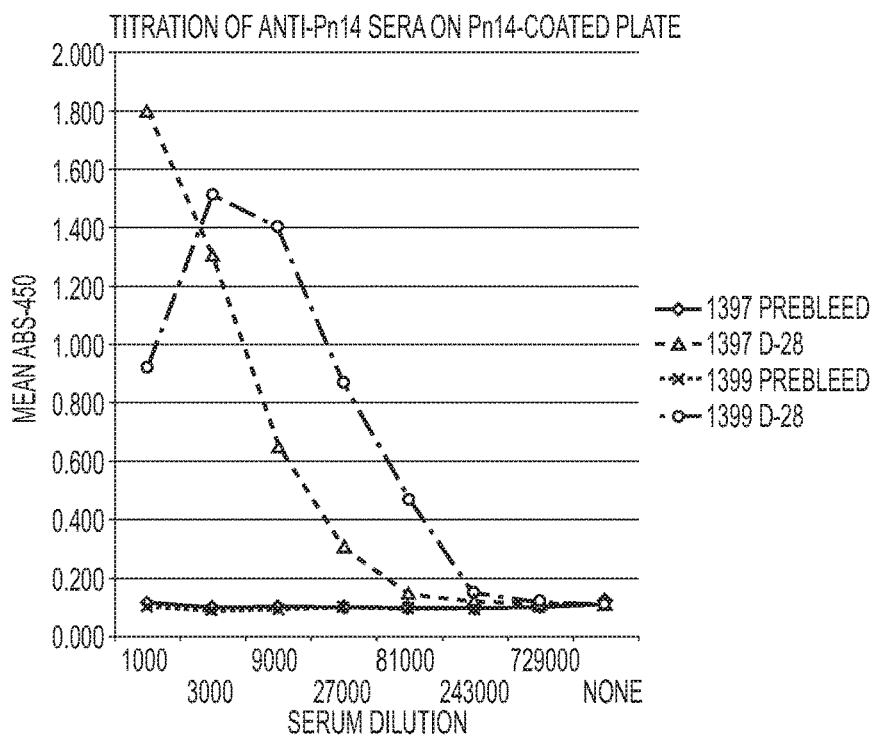

Sera was tested for reactivity by ELISA on a Brandtech Immunograde plate coated with 2 µg/ml of Pn6B or Pn14 (from ATCC) using gamma-specific detection. Results in FIG. 2 show a strong reactivity with Pn6B. Mouse 5086 was used for hybridoma production and three of the resulting hybridomas were used to prepare highly specific mouse anti-6B monoclonal antibodies. The results of the serum titration against Pn14 coated plates are shown in FIG. 3. Mouse 1397 was subsequently used for the production of four highly specific mouse monoclonal antibodies reactive with P14 polysaccharide. Unconjugated polysaccharide does not give a significant ELISA absorbance.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, containing and the like are not intended to be limiting. It is intended that the specification and examples be considered exemplary only with the true scope and spirit of the invention indicated by the following claims.

Sequences

```
CRM197
                                                      SEQ ID NO 1
GADDVVDSSK SFVMENFSSY HGTKPGYVDS IQKGIQKPKS GTQGNYDDDW

KEFYSTDNKY DAAGYSVDNE NPLSGKAGGV VKVTYPGLTK VLALKVDNAE

TIKKELGLSL TEPLMEQVGT EEFIKRFG DG ASRVVLSLPF AEGSSSVEYI

NNWEQAKALS VELEINFE TR GKRGQDAMYE YMAQACAGNR VRRSVGSSLS

CINLDWDVIR DKTKTKIESL KEHGPIKNKM SESPNKTVSE EKAKQYLE EF

HQTALEHPEL SELKTVTGTN PVFAGANYAA WAVNVAQVID SETADNLEKT

TAALSILPGI GS VMGIADGA VHHNTEEIVA QSIALSSLMV AQAIPLVGEL

VDIGFAAYNF VESIINLF QV VHNSYNRPAY SPGHKTQPFL HDGYAVSWNT VEDSIIRT

GF QGESGHDIKI TAENTPLPIA GVLLPTIPGK LDVNKSKT HI SVNGRKIRMR

CRAIDGDVTF CRPKSPVYVG NGVHANLH VA FHRSSSEKIH SNEISSDSIG

VLGYQKTVDH TKVNSKLS LF FEIKS

Domain of CRM197
                                                      SEQ ID NO 2
SPGHKTQPFL HDGYAVSWNT VEDSIIRT GF QGESGHDIKI TAENTPLPIA

GVLLPTIPGK LDVNKSKT HI SVNGRKIRMR CRAIDGDVTF CRPKSPVYVG

NGVHANLH VA FHRSSSEKIH SNEISSDSIG VLGYQKTVDH TKVNSKLS LF FEIKS

SEQ ID NO 3
GATATAC spacer

SEQ ID NO 4
GATATACCA spacer
```

-continued

SEQ ID NO 5

GATATACCATAT spacer

SEQ ID NO 6

XBBXBX putative heparin binding site

SEQ ID NO 7

GRKIRMRCR heparin binding site

Optimized CRM sequence
SEQ ID NO 8

ATGGGTGCTGATGATGTTGTTGATTCCTCTAAGTCTTTCGTGATGGAAAATTTCTCGT

CCTATCACGGTACCAAGCCTGGCTATGTGGATAGCATTCAAAAGGGTATTCAAAAAC

CGAAGTCTGGTACCCAGGGCAACTACGATGACGATTGGAAAGAGTTTTACAGCACC

GACAACAAATATGACGCGGCAGGCTACAGCGTTGATAATGAAAATCCGCTGAGCGG

TAAGGCTGGCGGCGTCGTTAAGGTTACCTATCCGGGTCTGACGAAAGTGCTGGCCCT

GAAAGTTGACAATGCTGAAACCATCAAAAAAGAACTGGGTCTGAGCTTGACCGAGC

CGCTGATGGAACAGGTTGGTACTGAAGAATTCATTAAACGTTTTGGTGACGGCGCGA

GCCGTGTTGTGCTGTCCCTGCCGTTTGCCGAGGGTTCTAGCTCCGTGGAGTATATCA

ACAATTGGGAACAGGCGAAAGCGTTGAGCGTCGAGCTGGAAATCAATTTCGAGACT

CGTGGTAAGCGTGGCCAAGATGCGATGTACGAGTACATGGCCCAGGCATGTGCGGG

TAACCGCGTCCGTCGCAGCGTCGGCAGCTCCCTGAGCTGCATTAACCTGGACTGGGA

CGTGATCCGCGACAAGACTAAGACCAAGATTGAGAGCCTGAAAGAGCACGGTCCGA

TTAAGAACAAAATGTCCGAGTCTCCGAACAAAACGGTGAGCGAAGAAAAAGCCAA

ACAGTATCTGGAAGAATTCCATCAGACCGCCCTGGAGCACCCAGAGCTGAGCGAGC

TGAAAACCGTCACCGGCACGAATCCGGTTTTTGCGGGTGCGAACTACGCGGCATGG

GCAGTCAATGTTGCGCAAGTCATCGACAGCGAAACGGCTGATAACTTGGAGAAAAC

CACCGCGGCACTGAGCATTCTGCCGGGCATCGGTAGCGTTATGGGCATTGCGGACG

GTGCCGTGCATCACAATACCGAAGAAATTGTCGCGCAGAGCATCGCATTGTCTAGCC

TGATGGTTGCACAGGCCATTCCGCTGGTAGGCGAATTGGTGGATATCGGTTTCGCGG

CTTACAATTTCGTTGAGTCGATCATTAACCTGTTTCAAGTCGTTCACAATAGCTATAA

CCGTCCGGCATACAGCCCGGGTCATAAGACGCAACCGTTTCTGCATGATGGCTATGC

CGTGAGCTGGAACACGGTCGAGGATTCGATTATCCGTACCGGTTTTCAGGGTGAGAG

CGGTCACGACATCAAAATCACCGCGGAGAACACGCCGCTGCCTATTGCGGGCGTCC

TGCTGCCGACGATCCCGGGCAAACTGGACGTTAACAAGAGCAAGACCCATATCAGC

GTCAACGGTCGTAAGATTCGCATGCGTTGTCGTGCAATCGACGGTGACGTGACGTTC

TGCCGCCCAAAAAGCCCGGTGTACGTGGGTAACGGCGTGCACGCGAATCTGCATGT

CGCGTTCCACCGCTCCTCAAGCGAGAAAATCCACAGCAATGAAATTAGCAGCGACA

GCATTGGTGTGTTGGGCTACCAAAAGACCGTGGATCACACCAAGGTTAATAGCAAG

CTGAGCCTGTTCTTTGAGATCAAAAGC

Not optimized CRM sequence

SEQ ID NO 9

ATGGGTGCCGATGACGTGGTTGACTCTTCCAAAAGCTTCGTCATGGAAAACTTCAGC

TCCTATCACGGCACTAAACCGGGTTATGTCGACAGCATCCAGAAAGGCATCCAGAA

ACCGAAATCTGGCACTCAGGGTAACTATGACGACGACTGGAAAGAGTTCTACTCTA

CCGACAACAAATACGACGCGGCTGGTTATTCTGTGGACAACGAAAACCCGCTGTCT

GGTAAAGCTGGTGGTGTTGTTAAAGTGACCTACCCGGGTCTGACCAAAGTTCTGGCT

-continued

```
CTGAAAGTGGACAACGCCGAAACCATCAAAAAAGAACTGGGTCTGTCTCTGACCGA
ACCGCTGATGGAACAGGTAGGTACCGAGGAATTCATCAAACGTTTTGGTGATGGTG
CGTCCCGTGTTGTACTGTCTCTGCCATTTGCCGAAGGTTCTAGCTCTGTCGAGTACAT
CAACAACTGGGAGCAGGCCAAAGCTCTGTCTGTGGAACTGGAAATCAACTTCGAGA
CCCGTGGTAAACGTGGTCAGGACGCAATGTATGAATACATGGCACAGGCTTGCGCG
GGTAACCGTGTACGTCGTTCTGTAGGTTCTTCCCTGTCTTGCATCAACCTGGACTGGG
ATGTCATCCGTGACAAAACCAAAACCAAAATCGAGTCCCTGAAAGAGCACGGTCCG
ATCAAAAACAAAATGAGCGAATCTCCGAACAAAACGGTCTCTGAGGAAAAAGCGA
AACAGTACCTGGAAGAATTCCATCAGACCGCCCTGGAACACCCGGAACTGTCTGAA
CTGAAAACCGTTACCGGTACTAACCCGGTTTTCGCAGGTGCTAACTACGCAGCGTGG
GCGGTTAACGTAGCCCAGGTAATCGATTCCGAAACCGCAGACAACCTGGAAAAAAC
GACTGCGGCTCTGTCTATTCTGCCGGGTATTGGTAGCGTGATGGGTATTGCAGATGG
TGCAGTTCACCACAACACGGAAGAAATCGTTGCGCAGTCTATCGCTCTGTCTTCTCT
GATGGTAGCACAGGCGATCCCGCTGGTTGGTGAACTGGTTGACATTGGCTTCGCGGC
CTACAACTTCGTTGAATCCATCATCAACCTGTTCCAGGTTGTGCACAACTCTTACAAC
CGTCCAGCTTACTCTCCGGGTCACAAAACCCAGCCGTTCCTGCACGACGGTTATGCG
GTTTCTTGGAACACCGTTGAAGACAGCATCATCCGTACTGGTTTCCAGGGTGAATCT
GGCCACGACATCAAAATCACTGCTGAAAACACCCCGCTGCCGATCGCAGGTGTTCTC
CTGCCAACTATTCCGGGTAAACTGGACGTGAACAAATCCAAAACGCACATCTCCGT
GAACGGTCGTAAAATCCGCATGCGTTGTCGTGCGATTGATGGTGACGTTACTTTCTG
TCGTCCGAAATCTCCGGTCTACGTAGGTAACGGTGTACATGCTAACCTCCATGTAGC
GTTCCACCGTTCTTCTTCCGAGAAAATCCACTCCAACGAGATCTCTAGCGACTCTAT
CGGTGTTCTGGGTTACCAGAAAACCGTTGACCACACCAAAGTGAACTCCAAACTCA
GCCTGTTCTTCGAAATCAAATCT
``` crm 7                                                 SEQ ID NO 10

GAGCTCTAAGAAGGA<u>GATATAC</u>ATGGGTGCCGATGACGTGGTTGACTCT crm 7_2                                               SEQ ID NO 11

GAGCTCTTAAGAAGGA<u>GATATAC</u>ATGGGTGCCGATGACGTGGTTGACTCT crm 8                                                 SEQ ID NO 12

GAGCTCTAAGAAGGA<u>GATATACA</u>ATGGGTGCCGATGACGTGGTTGACTCT crm 9                                                 SEQ ID NO 13

GAGCTCTAAGAAGGA<u>GATATACAC</u>ATGGGTGCCGATGACGTGGTTGACTCT crm 12                                                SEQ ID NO 14

GAGCTCTAAGAAGGA<u>GATATACCATATA</u>TGGGTGCCGATGACGTGGTTGACTCT

SEQ ID NO 15

TCTAGAAATAATTTTGTTTAACTTTAAGAAGGAGATATACATATGGCTAGCATGACT

GGTGGACAGCAAATGGGTCGGGATCCGAATTCGAGCTCTAAGAAGGAGATATACC

SEQ ID NO 16

TCTAGAAATAATTTTGTTTAACTTTAAGAAGGAGATATACATATGGCTAGCATGACT

GGTAAGGAGATATACC

-continued

SEQ ID NO 17

TCTAGAAATAATTTTGTTTAACTTTAAGAAGGAGATATACATATGGCTAGCATGACT

GGTGCGMAYCCATTCAGTGAAGAAGRAGSTTYATTT

---

The invention claimed is:

1. A method of producing a CRM protein comprising: providing a recombinant cell that contains an expression vector, wherein the recombinant cell has a reduced activity of one or more disulfide reductase enzymes that shifts the redox status of the cytoplasm to a more oxidative state as compared to an unmodified recombinant cell, and the expression vector contains a promoter functionally linked to a CRM coding sequence; inducing the expression vector to produce CRM protein cytoplasmically; and isolating the CRM protein expressed, wherein the CRM protein expressed is soluble.

2. The method of claim 1, wherein the expression vector contains a ribosome binding site, an initiation codon, and an expression enhancer region upstream of the CRM coding sequence.

3. The method of claim 2, wherein the expression vector contains at least one spacer between the ribosome binding site and the initiation codon.

4. The method of claim 1, wherein the soluble CRM protein expressed comprises natively folded protein.

5. The method of claim 1, wherein the promoter is an inducible promoter.

6. The method of claim 1, wherein the recombinant cell is propagated at a temperature from about 15° C. to about 37° C.

7. The method of claim 1, wherein the CRM protein is isolated by chromatography.

8. The method of claim 7, wherein the chromatography comprises a sulfate resin, a gel resin, an active sulfated resin, a phosphate resin, a heparin resin or a heparin-like resin.

9. A method of producing a CRM protein comprising: providing a recombinant cell that contains an expression vector, wherein the recombinant cell has a reduced activity of one or more disulfide reductase enzymes and the expression vector contains a promoter functionally linked to a CRM coding sequence, wherein the one or more disulfide reductase enzymes comprises one or more of an oxidoreductase, a dihydrofolate reductase, a thioredoxin reductase or a glutathione reductase; expressing CRM protein from the CRM coding sequence cytoplasmically; and isolating the CRM protein expressed, wherein the CRM protein expressed is soluble.

10. The method of claim 9, wherein the recombinant cell is an E. coli cell or a derivative or strain of E. coli.

11. The method of claim 9, wherein reduced activity of the one or more disulfide reductase enzymes shifts the redox state of the cytoplasm of the recombinant cell to an oxidative state as compared with a non-recombinant cell.

12. The method of claim 9, wherein the CRM coding sequence encodes one or more CRM epitopes, CRM peptide sequences, CRM domains, or combinations thereof.

13. The method of claim 9, wherein the CRM coding sequence encodes $CRM_{197}$.

14. The method of claim 9, wherein the expression vector contains a spacer.

15. The method of claim 9, wherein the promoter is a constitutive promoter.

16. The method of claim 9, wherein the expression vector comprises a ribosome binding site upstream of the CRM coding sequence and an ATG codon.

17. The method of claim 9, wherein the soluble CRM protein expressed comprises natively folded protein.

18. The method of claim 9, wherein the promoter is an inducible promoter.

19. The method of claim 9, wherein the recombinant cell is propagated at a temperature from about 15° C. to about 37° C.

20. The method of claim 9, wherein the CRM protein is isolated from the cell by chromatography.

21. The method of claim 20, wherein the chromatography comprises a sulfate resin, a gel resin, an active sulfated resin, a phosphate resin, a heparin resin or a heparin-like resin.

22. The method of claim 9, further comprising conjugating the isolated CRM protein.

23. The method of claim 22, wherein the conjugated CRM protein is a vaccine.

24. A method of producing a CRM protein comprising: providing a recombinant cell that contains an expression vector, wherein the expression vector contains a promoter functionally linked to a CRM coding sequence, wherein the recombinant cell has reduced activity of one or more disulfide reductase enzymes; expressing CRM protein from the CRM coding sequence cytoplasmically; and isolating the CRM protein expressed, wherein the CRM protein expressed is soluble and comprises native disulfide bonds.

25. The method of claim 24, wherein the recombinant cell is a prokaryotic or a eukaryotic cell.

26. The method of claim 25, wherein the prokaryotic cell is an E. coli cell or a derivative or strain of E. coli.

27. The method of claim 24, wherein the promoter is constitutive or inducible.

28. The method of claim 24, wherein the CRM coding sequence encodes one or more CRM epitopes, CRM peptide sequences, CRM domains, or combinations thereof.

29. The method of claim 24, wherein the CRM coding sequence encodes $CRM_{197}$.

30. The method of claim 24, wherein the recombinant cell has been modified to shift the redox status of the cytoplasm to a more oxidative state as compared to an unmodified recombinant cell.

31. The method of claim 24, wherein the one or more disulfide reductase enzymes comprises one or more of an oxidoreductase, a dihydrofolate reductase, a thioredoxin, a thioredoxin reductase or a glutathione reductase.

32. The method of claim 24, wherein the expression vector contains a spacer sequence between a ribosome binding site and an initiation codon.

33. The method of claim 24, wherein the expression vector contains an expression enhancer.

34. The method of claim 33, wherein the expression enhancer comprises a ribosome binding site upstream of the CRM coding sequence and an initiation codon.

35. The method of claim 24, wherein isolating comprises:
loading the CRM protein onto a chromatography column containing a resin with a loading buffer;
washing the resin with one or more washing buffers; and
eluting CRM protein from the resin with an elution buffer.

36. The method of claim 35, wherein the loading buffer and the washing buffer are the same.

37. The method of claim 35, wherein the loading buffer and the one or more washing buffers are low conductivity buffers that have a conductivity of about 10 mS/cm or less.

38. The method of claim 35, wherein the elution buffer is a high conductivity buffer with a conductivity of about 10 mS/cm or more.

39. The method of claim 35, wherein the resin is selected from the group consisting of a sulfate resin, a gel resin, an active sulfated resin, a phosphate resin, a heparin resin or a heparin-like resin.

* * * * *